US00PP22840P2

(12) United States Plant Patent
Jones

(10) Patent No.: US PP22,840 P2
(45) Date of Patent: Jul. 3, 2012

(54) ***NEMESIA* PLANT NAMED 'SUNJONBUHO'**

(50) Latin Name: ***Nemesia denticulata*×*Nemesia caerulea***
Varietal Denomination: Sunjonbuho

(75) Inventor: Jimmy Jones, St. Brides Netherwent (GB)

(73) Assignee: Suntory Flowers Ltd., Tokyo (JP)

( * ) Notice: Subject to any disclaimer, the term of this patent is extended or adjusted under 35 U.S.C. 154(b) by 27 days.

(21) Appl. No.: 12/927,116

(22) Filed: Nov. 5, 2010

(51) Int. Cl.
*A01H 5/00* (2006.01)

(52) U.S. Cl. ..... Plt./458

(58) Field of Classification Search ..... Plt./458
See application file for complete search history.

*Primary Examiner* — June Hwu
(74) *Attorney, Agent, or Firm* — C. A. Whealy

(57) ABSTRACT

A new and distinct cultivar of *Nemesia* plant named 'Sunjonbuho', characterized by its upright and mounded growth habit; freely branching habit; freely flowering habit; long flowering period; purple, purple violet and violet-colored fragrant flowers; and good garden performance.

1 Drawing Sheet

Botanical designation: *Nemesia denticulata*×*Nemesia caerulea.*

Cultivar denomination: 'SUNJONBUHO'.

BACKGROUND OF THE INVENTION

The present invention relates to a new and distinct cultivar of *Nemesia* plant, botanically known as *Nemesia denticulata*×*Nemesia caerulea* and hereinafter referred to by the name 'Sunjonbuho'.

The new *Nemesia* plant is a product of a planned breeding program conducted by the Inventor in St. Brides Netherwent, Monmouthshire, Wales. The objective of the breeding program is to create new mounding and freely-branching *Nemesia* plants with unique and attractive flower coloration.

The new *Nemesia* plant originated from a cross-pollination made by the Inventor in June, 2007 in St. Brides Netherwent, Monmouthshire, Wales of a proprietary selection of *Nemesia denticulata*×*Nemesia caerulea* identified as code number 7NEY1, not patented, as the female, or seed, parent with a proprietary selection of *Nemesia denticulata*×*Nemesia caerulea* identified as code number 7NEKF, not patented, as the male, or pollen, parent. The new *Nemesia* plant was discovered and selected by the Inventor as a single flowering plant within the progeny of the stated cross-pollination in a controlled greenhouse environment in St. Brides Netherwent, Monmouthshire, Wales in April, 2008.

Asexual reproduction of the new *Nemesia* plant by vegetative cuttings in a controlled environment in St. Brides Netherwent, Monmouthshire, Wales since May, 2008, has shown that the unique features of this new *Nemesia* plant are stable and reproduced true to type in successive generations.

SUMMARY OF THE INVENTION

Plants of the new *Nemesia* have not been observed under all possible environmental conditions. The phenotype may vary somewhat with variations in environment such as temperature and light intensity without, however, any variance in genotype.

The following traits have been repeatedly observed and are determined to be the unique characteristics of 'Sunjonbuho'.

These characteristics in combination distinguish 'Sunjonbuho' as a new and distinct cultivar of *Nemesia* plant:

1. Upright and mounded growth habit.
2. Freely branching habit.
3. Freely flowering habit.
4. Long flowering period.
5. Purple, purple violet and violet-colored fragrant flowers.
6. Good garden performance.

Plants of the new *Nemesia* can be compared to plants of the female parent selection. Plants of the new *Nemesia* differ primarily from plants of the female parent selection in flower color as plants of the female parent selection have light blue-colored flowers.

Plants of the new *Nemesia* can be compared to plants of the male paren selection. Plants of the new *Nemesia* differ primarily from plants of the male parent selection in flower color as plants of the male parent selection have purple and white bi-colored flowers.

Plants of the new *Nemesia* can also be compared to plants of 'Aqua Blue', not patented. In side-by-side comparisons conducted by the Inventor in Higashiomi, Shiga, Japan, plants of the new *Nemesia* differed from plants of 'Aqua Blue' in the following characteristics:

1. Plants of the new *Nemesia* were smaller than plants of 'Aqua Blue'.
2. Plants of the new *Nemesia* had larger flowers than plants of 'Aqua Blue'.
3. Flowers of plants of the new *Nemesia* were more fragrant than flowers of plants of 'Aqua Blue'.
4. Plants of the new *Nemesia* and 'Aqua Blue' differed in flower color as plants of 'Aqua Blue' had light blue-colored flowers.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph at the top of the sheet comprises a side perspective view of a typical flowering plant of 'Sunjonbuho' grown in a container.

The photograph at the bottom of the sheet is a close-up view of typical flowers of 'Sunjonbuho'.

DETAILED BOTANICAL DESCRIPTION

The aforementioned photographs and following observations, measurements and values describe plants grown during the winter in 15-cm containers in a glass-covered greenhouse in Higashiomi, Shiga, Japan and under commercial practice. During the production of the plants, day temperatures averaged 15° C. and night temperatures averaged 5° C. Plants were four months old when the photographs and description were taken. In the following description, color references are made to The Royal Horticultural Society Colour Chart, 2007 Edition, except where general terms of ordinary dictionary significance are used.

Botanical classification: *Nemesia denticulata*×*Nemesia caerulea* 'Sunjonbuho'.

Parentage:

*Female, or seed, parent*.—Proprietary selection of *Nemesia denticulata*×*Nemesia caerulea* identified as code number 7NEY1, not patented.

*Male, or pollen, parent*.—Proprietary selection of *Nemesia denticulata*×*Nemesia caerulea* identified as code number 7NEKF, not patented.

Propagation:

*Type*.—By vegetative cuttings.

*Time to initiate roots*.—About one week at temperatures of 20° C. to 25° C.

*Time to produce a rooted young plant*.—About 20 days at temperatures of 15° C. to 20° C.

*Root description*.—Fibrous; white in color.

*Rooting habit*.—Freely branching; moderately dense.

Plant description:

*Plant and growth habit*.—Upright and mounded growth habit; freely branching with two lateral branches potentially forming at every node; moderately vigorous growth habit.

*Plant height*.—About 19.8 cm.

*Plant diameter*.—About 25.6 cm.

Lateral branch description:

*Length*.—About 18.4 cm.

*Diameter*.—About 1.7 mm.

*Internode length*.—About 1.4 cm.

*Aspect*.—Mostly upright.

*Texture*.—Smooth, glabrous.

*Color*.—Close to 144A.

Foliage description:

*Arrangement*.—Opposite, simple.

*Length*.—About 3.5 cm.

*Width*.—About 1.5 cm.

*Shape*.—Lanceolate.

*Apex*.—Acute.

*Base*.—Obtuse to rounded.

*Margin*.—Shallowly serrate.

*Texture, upper and lower surfaces*.—Smooth, glabrous.

*Venation pattern*.—Pinnate, reticulate.

*Color*.—Developing and fully expanded leaves, upper surface: Close to 137A; venation, close to 144A. Developing and fully expanded leaves, lower surface: Close to 138B; venation, close to 144B.

*Petioles*.—Length: About 4.6 mm. Diameter: About 0.6 mm. Texture, upper and lower surfaces: Smooth, glabrous. Color, upper and lower surfaces: Close to 144A.

Flower description:

*Flower arrangement and habit*.—Bilabiate solitary flowers arranged on terminal racemes; flowering acropetally towards the apex; flowers facing mostly outwardly; freely flowering habit with about eleven flowers per raceme and about 47 racemes developing per plant.

*Fragrance*.—Fragrant; pleasant. Natural flowering season: In Japan, plants flower naturally from early spring to early summer; flowering continuous during this period; early flowering habit, flowers begin flowering about three months after planting.

*Flower longevity*.—Flowers last about five to seven days on the plant; flowers not persistent.

*Inflorescence diameter*.—About 4.5 cm.

*Flower size* (*diameter by length*).—About 2.3 cm by 2.1 cm.

*Flower depth*.—About 1.4 cm.

*Flower buds*.—Shape: Obovate. Length: About 11.1 mm. Diameter: About 6.5 mm Color: Close to 77C.

*Petals*.—Arrangement: Five modified petals; four upper petals fused forming an upright lobed and arched banner lip; lower petal modified into a larger lip with convex oval protuberance serving as a nectar guide and insect landing platform. Shape, upper lip: Elliptic. Shape, lower lip: Reniform. Apex, upper lip: Rounded. Apex, lower lip: Cordate. Margin, upper lip: Entire; undulate. Margin, lower lip: Entire; undulate. Length, upper lip: About 12.1 mm. Length, lower lip: About 10.5 mm. Width, upper lip: About 7 mm to 9 mm. Width, lower lip: About 17.6 mm. Texture, upper and lower lips, upper and lower surfaces: Smooth, glabrous. Color, upper lip: When opening, upper surface: Close to 70B; towards the throat, fine lines, close to N88A. When opening, lower surface: Close to 77D. Fully opened, upper surface: Close to N77B and N82C; towards the throat, close to N87B and N88B with fine lines, close to N88A. Fully opened, lower surface: Close to N82D. Color, lower lip: When opening, upper surface: Close to 76B overlain with streaks, close to 75A; nectar guide, close to 5B. When opening, lower surface: Close to N82C. Fully opened, upper surface: Close to N77B and N82C; towards the margins, close to 84B to 84D; nectar guide, close to 5D; with development, color becoming closer to 155B and towards the margins, close to 84D. Fully opened, lower surface: Close to N82D.

*Spur*.—Length: About 7.8 mm. Diameter: About 1.4 mm. Color: Close to 145C.

*Sepals*.—Arrangement: Calyx star-shaped with five sepals fused at the base. Shape: Lanceolate. Apex: Acute. Margin: Entire. Length: About 4.2 mm. Width: About 1.7 mm. Texture, upper and lower surfaces: Smooth, glabrous. Color, upper and lower surfaces: Close to 143B.

*Peduncles*.—Length: About 4.3 cm. Diameter: About 1.5 mm. Strength: Moderately strong; flexible. Texture: Smooth, glabrous. Color: Close to 144A.

*Pedicels*.—Length: About 12.2 mm. Diameter: About 0.4 mm. Strength: Moderately strong; flexible. Texture: Smooth, glabrous. Color: Close to 144A.

*Reproductive organs*.—Stamens: Quantity/arrangement: Four per flower. Stamen length: About 1 mm to 3 mm. Anther shape: Narrowly elliptic. Anther size: About 1 mm by 0.5 mm. Anther color: Close to 9B. Pollen amount: Moderate. Pollen color: Close to 9A. Pistils: Quantity: One per flower. Pistil length: About 2.3 mm. Stigma shape: Ovate. Stigma color: Close to 160C. Ovary color: Close to 144C. Seed/fruit: Seed and fruit development have not been observed on plants of the new *Nemesia*.

Pathogen/pest resistance: Plants of the new *Nemesia* have not been observed to be resistant to pests and pathogens common to *Nemesia*.

Garden performance: Plants of the new *Nemesia* have been observed have good garden performance and to tolerate wind, rain and temperatures ranging from 5° C. to 35° C.

It is claimed:

1. A new and distinct *Nemesia* plant named 'Sunjonbuho' as illustrated and described.

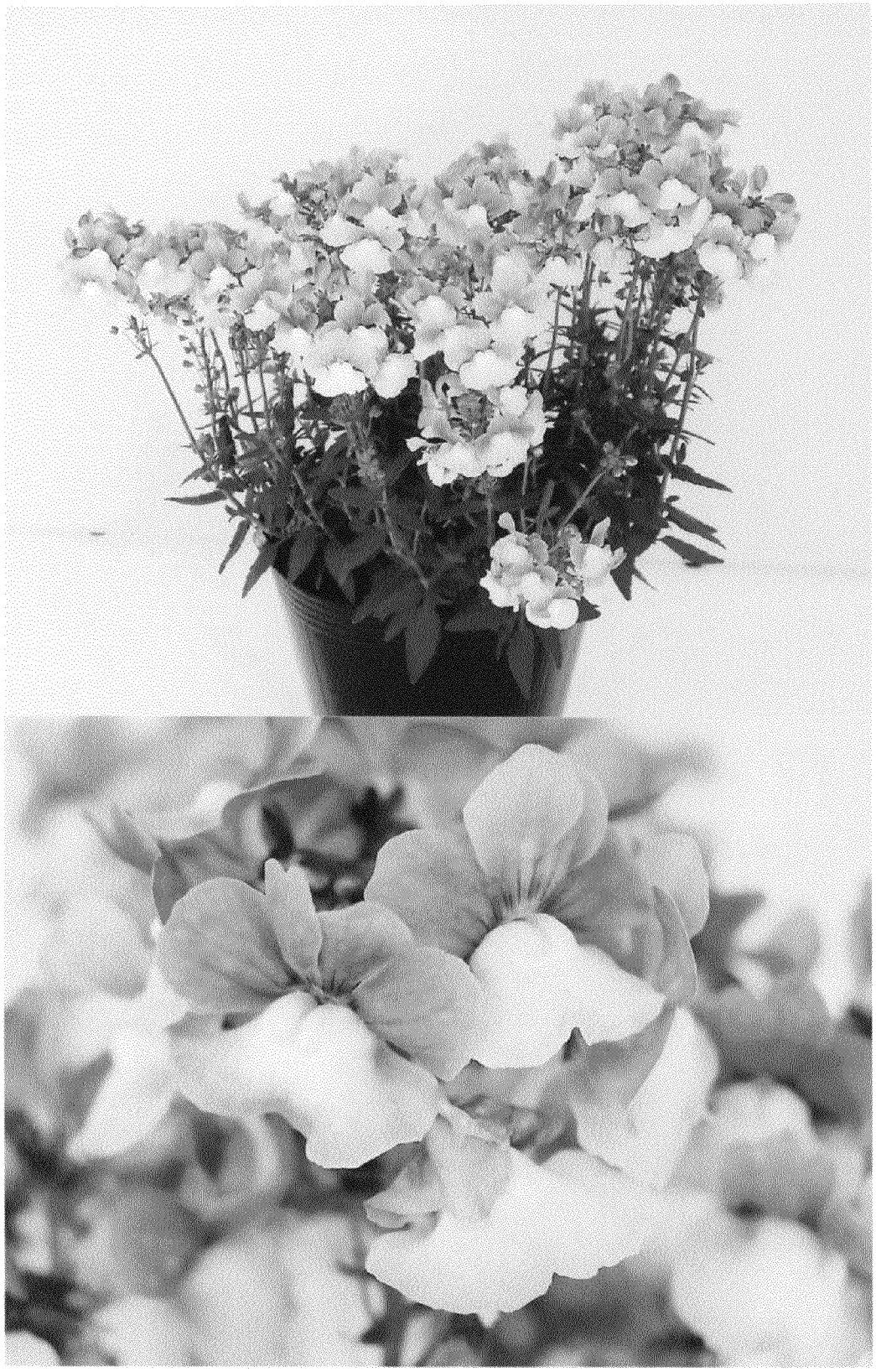

* * * * *